US006740214B1

(12) United States Patent
Dobson et al.

(10) Patent No.: US 6,740,214 B1
(45) Date of Patent: May 25, 2004

(54) MICROELECTRODE BIOSENSOR AND METHOD THEREFOR

(75) Inventors: Peter James Dobson, Oxford (GB); Peter Alexander Leigh, Oxford (GB); Yasue Nakagawa, Oxford (GB); Hugh Allen Oliver Hill, Oxford (GB)

(73) Assignee: ISIS Innovation Limited, Oxford (GB)

( * ) Notice: Subject to any disclaimer, the term of this patent is extended or adjusted under 35 U.S.C. 154(b) by 0 days.

(21) Appl. No.: 09/674,991

(22) PCT Filed: May 7, 1999

(86) PCT No.: PCT/GB99/01425

§ 371 (c)(1),
(2), (4) Date: Mar. 12, 2001

(87) PCT Pub. No.: WO99/58966

PCT Pub. Date: Nov. 18, 1999

(30) Foreign Application Priority Data

May 8, 1998 (GB) .............................................. 9809918

(51) Int. Cl.$^7$ ......................... G01N 27/327; B05D 3/00
(52) U.S. Cl. .............................. 204/403.1; 204/403.01; 204/403.14; 427/2.13
(58) Field of Search ....................... 204/403.01, 403.04, 204/403.05, 403.07, 403.09, 403.1, 403.13, 403.14, 403.08; 427/2.13

(56) References Cited

U.S. PATENT DOCUMENTS 4,908,115 A    3/1990   Morita et al. ............... 204/294

5,328,847 A *  7/1994   Case et al. ................. 205/778

FOREIGN PATENT DOCUMENTS

EP    0 653 629 A2    5/1995
GB    2 217 461 A    10/1989

* cited by examiner

Primary Examiner—Alex Noguerola
(74) Attorney, Agent, or Firm—Wolf, Greenfield & Sacks, P.C.

(57) ABSTRACT

There is disclosed a biosensor comprising a conducting surface, a layer of dielectric material overlying the conducting surface, a plurality of micro electrodes constituted by a plurality of pores extending through the thickness of said dielectric layer, a biopolymer positioned on the conducting surface in said pores, and a counter electrode arranged such that electrical connection can be made between it and at least part of said conducting surface by a fluid to be assessed. Such a device can be made using a method comprising the steps of providing a conducting surface;

providing a layer of dielectric material adjacent to said conducting surface, said dielectric material comprising a plurality of pores extending through the thickness of the dielectric layer;

providing a biopolymer on the conducting surface in said pores; and providing a counter electrode insulated from said conducting surface.

24 Claims, 3 Drawing Sheets

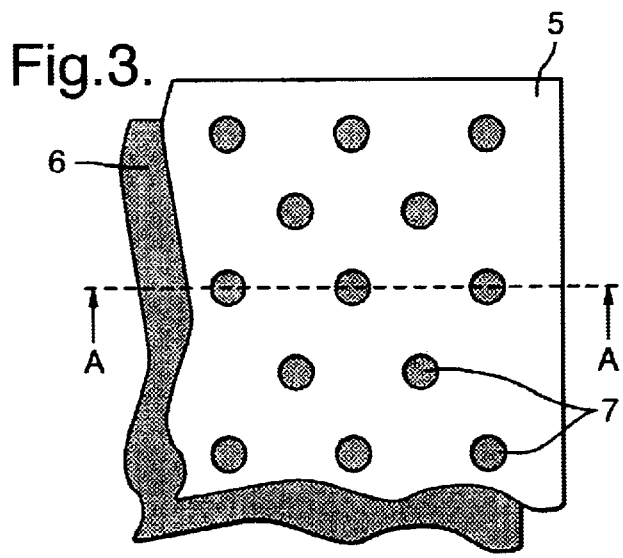
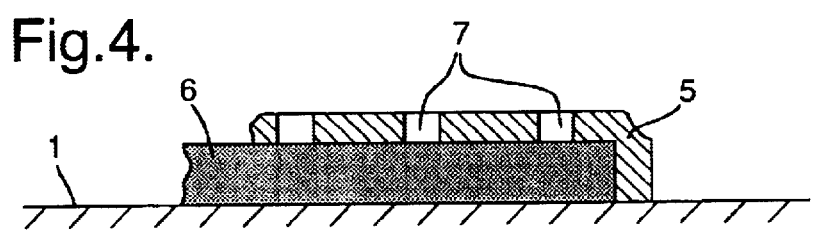
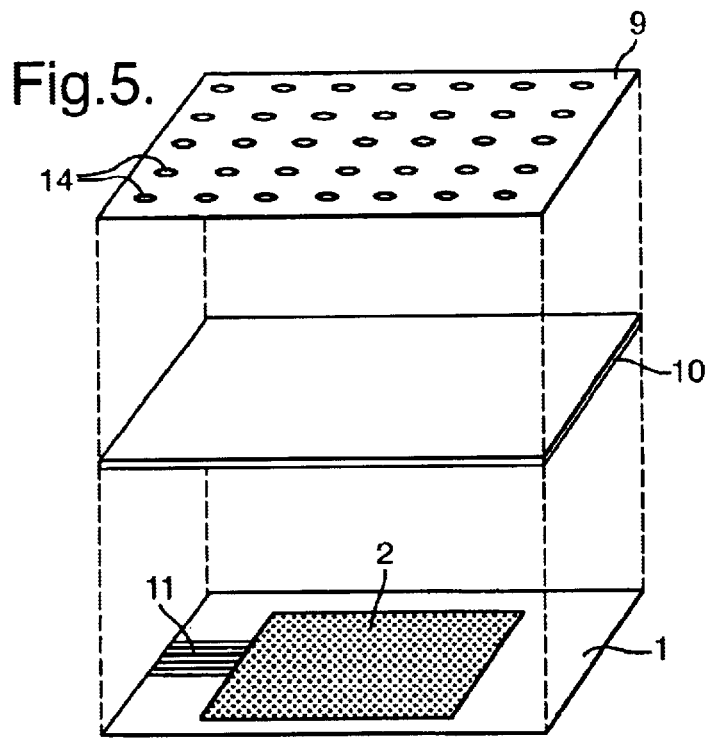

MICROELECTRODE BIOSENSOR AND METHOD THEREFOR

This application is the National Stage of International Application No. PCT/GB99/01425, filed May 7, 1999.

BACKGROUND OF THE INVENTION

This invention relates to the use of micro-electrode arrays in biosensors and to methods of producing such biosensors.

An array of micro electrodes offers many advantages over a large area electrode for use as an amperometric electrochemical sensor. These advantages include a very small charging capacitance, radial diffusion kinetics, a rapid response time and easily interpreted current-voltage behaviour. The present invention relates to a particular arrangement of such an array to provide a biosensor.

The present invention provides a biosensor comprising a conducting surface, a layer of dielectric material overlying the conducting surface, a plurality of micro electrodes constituted by a plurality of pores extending through the thickness of said dielectric layer, each pore being separated from its neighbour, a biopolymer positioned in said pores, and a counter electrode arranged such that electrical connection can be made between it and at least part of said conducting surface by a fluid to be assessed.

SUMMARY OF THE INVENTION

The present invention also provides a method of making a biosensor comprising the steps of:
  providing a conducting surface;
  providing a layer of dielectric material adjacent to said conducting surface, said dielectric material comprising a plurality of pores extending through the thickness of the dielectric layer, each pore being separated from its neighbour;
  providing a biopolymer in said pores, and
  providing a counter electrode insulated from said conducting surface.

In general, the biosensor comprises one or more areas of conducting material arranged on an insulating substrate. Adjacent to each area of conducting material is a dielectric coating which comprises a plurality of pores. These pores are the micro electrodes that convert a chemical response into an electrical signal. They do this due to the presence of a biopolymer immobilised on the conducting surface. In use, a fluid to be assessed is applied to the pores in the dielectric surface so as to be in contact with the biopolymer immobilised in the pores. A counter electrode is also provided so as to be in electrical connection with at least one of the conducting areas via the fluid being assessed. A constant voltage may be applied between the counter electrode and the conducting area and the current that flows therebetween may be measured. Any such measured current is indicative of the amount of a chosen compound in the assessed fluid. Different biopolymers may be used to allow different compounds to be measured giving great flexibility. The biosensor device typically has dimensions of a few millimeters although it could of course be made smaller or larger, depending on the intended application.

The electrodes typically have areas of 1 to 100 $\mu m^2$ and are typically separated by distances of about ten times their diameter. The surface of the electrode can be functionalised with various biopolymers, especially enzymes such that they will only give an electrochemical response to a specific compound (or analyte). Other biopolymers include other proteins, as well as nucleic acids, lipids and polysaccharides. For example, enzymes that respond to important body fluid components such as lactate, glucose, creatine, or various antibodies could be used. Typical enzymes include lactate dehydrogenase, glucose dehydrogenase, cytochrome P450 and mutants of the aforesaid enzymes. In addition by ociation of these enzymes, antibodies, nucleic acids, lipids and polysaccharides can be made electrochemically active. Micro-electrode arrays have not, it is believed, previously been activated by biopolymers for use as biosensors. One advantage is that only two electrodes are required vis the working electrode and a counter electrode. Although the magnitude of the current from an individual micro-electrode is low, this can be offset by an improved signal to noise ratio if an array of hundreds or thousands of individual micro-electrodes is used. This is because the signal to noise ratio increases as the square root of the number of individual micro-electrodes.

Reference will now be made, by way of non-limitative example, to the accompanying drawings in which:

BRIEF DESCRIPTION OF THE DRAWINGS

FIG. 3 is a plan view of part of a micro-electrode array.

FIG. 4 is a sectional side view along the line A—A in FIG. 3.

FIG. 5 is an exploded perspective view of a biosensor according to a third embodiment.

DETAILED DESCRIPTION OF THE INVENTION

Figure 1:
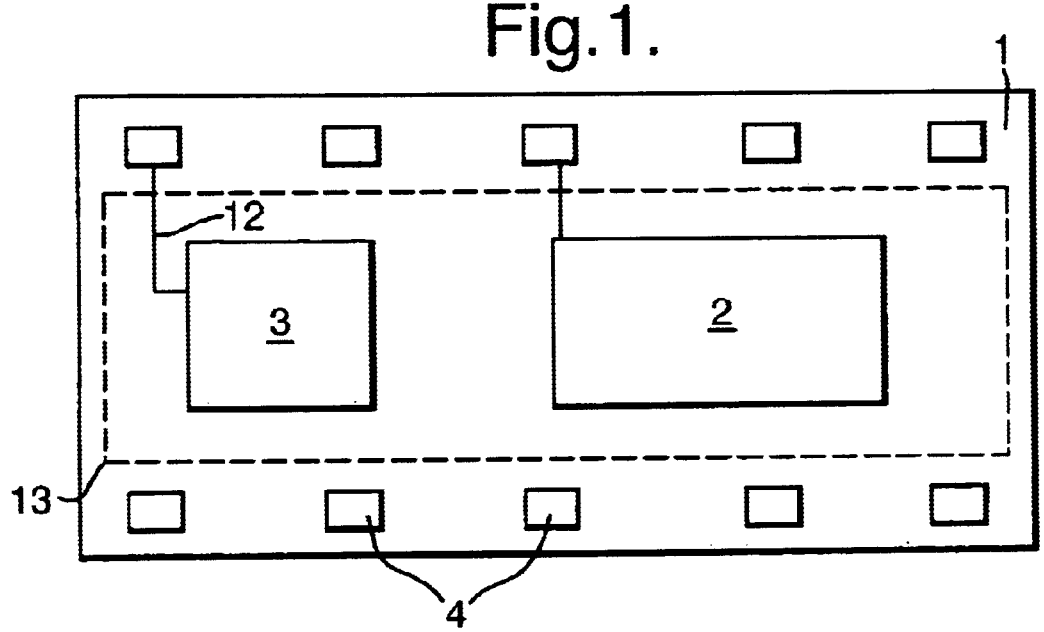
FIG. 1 is a plan view of a biosensor according to a first embodiment of the invention.

FIGS. 1, 3 and 4 show a first embodiment of the invention. This embodiment is a compact device of size comparable to an integrated circuit package which exploits the advantages of micro-electrode sensors with the specificity brought about by biopolymer coating of the electrode surfaces. An insulating substrate 1 has attached to it a conducting patch or area 6 as shown in FIG. 3. The insulating substrate is preferably silicon. The patch 6 could in general be of any conducting material but is preferably carbonaceous.

Upon the patch 6 is a layer of dielectric material 5 which has a plurality of pores 7 passing therethrough. The dielectric layer is preferably 0.1–0.8 $\mu m$ thick. The pores 7 present in this coating layer reveal the carbon surface 6 beneath it. This array of pores constitutes an array of micro-electrodes. The conducting layer 6 and dielectric layer 5 are together denoted by the numeral 2 in FIG. 1.

Each pore advantageously has a diameter or diagonal (if square) of dimensions in the range 1 to 10 $\mu m$, although pores down to, say, 0.2 $\mu m$ are possible. Individual pores are desirably separated by a distance of 10–100 $\mu m$ to ensure that each micro-electrode behaves independently of its neighbours. Thus the patch 2 may comprise hundreds or even thousands of micro-electrodes.

The insulating substrate may be mounted on to a standard integrated circuit carrier (not shown) and wire bond connections 12 may be made between bonding pads 4 on the insulating substrate and output pins on the carrier (not shown).

As shown in FIG. 1, a counter electrode 3 is attached to the insulating substrate so that when a fluid sample to be analyzed is placed on the biosensor, a connection is formed between the conducting surface 6 and counter electrode 3.

In order for the biosensor to provide results about the presence of a specific compound, the pores are "functionalised" with a biopolymer.

The biopolymer is chosen to convert a biochemical response in a liquid sample into a quantifiable and processable electrical signal. In some cases, it is desirable to provide a permeable membrane (not shown) to cover the assembly.

The top working surface of the device is surrounded by a small polymer wall 13 such that a drop of liquid sample can be placed over the pores and retained in them.

Figure 2:
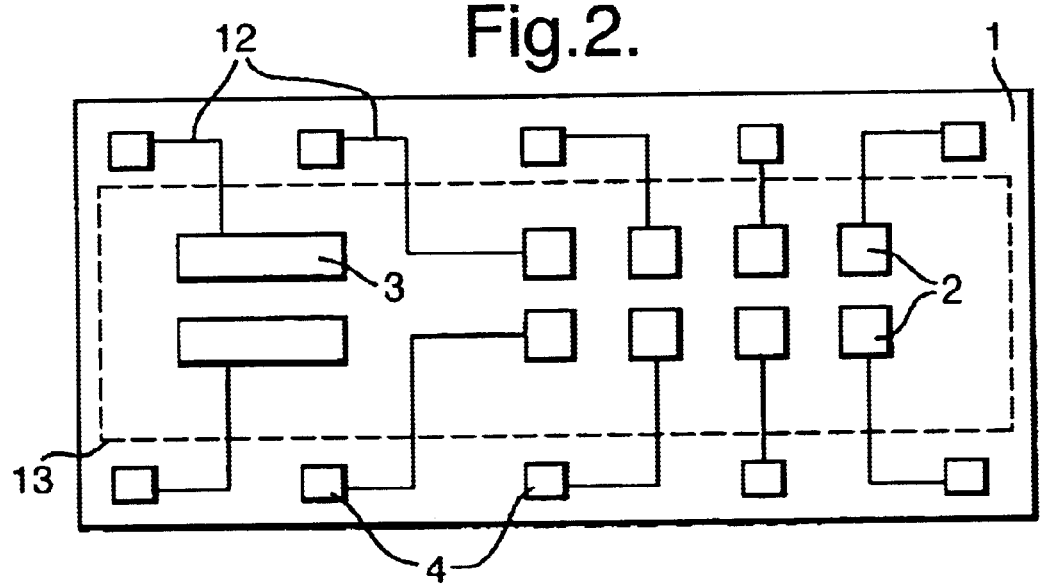
FIG. 2 is a plan view of a biosensor according to a second embodiment of the invention.

FIG. 2 shows a second embodiment of the invention. In most respects the structure is identical to that of FIG. 1. However, here there are two counter electrodes 3 and eight 2 mm square patches of micro electrodes 2.

A third embodiment of the invention is shown in FIG. 5. This embodiment is particularly suited to applications where a compound to be assessed is excreted through the skin, for example perspiration. Lower layer 1 of FIG. 5 may consist of a thin conducting film deposited onto a plastic substrate. Typically the substrate is made of a silicone polymer or PET (polyethylene terephthalate) and the conducting film is carbon based. An electrical connection 11 to this base layer is preferably made at the edge of the structure. The conducting film has thereover a holey insulating dielectric layer 5, as in the previous two embodiments.

The second layer 10 is a porous membrane or layer to provide a "reservoir" for retaining the analyte, and to provide a "spacer" between the functionalised electrode and the counter electrode. This layer can be made from any suitable material, ranging from a thin cellulose filter paper to a thicker fibrous polymer mat. In use, the layer retains the analyte as it is assessed.

The upper layer 9 of FIG. 5 is a perforated conducting layer or sheet, typically a metal coated plastic film. The perforations 14 permit the infusion of the liquid that is to be analyzed. These should be of sufficient size to permit capillary infusion, but not so large as to permit damage to the integrity of the structure. These perforations 14 could also perform a secondary function, namely to keep large cellular structures from interfering with the electrochemical cell. The perforations 14 may advantageously be produced using a suitable spiked roller. The size of these holes will typically vary from 1 micron diameter to (say) 100 microns. Electrical connection may be made to the metal under surface of the film. The metal could be gold, or any other appropriate metal. It could be advantageous to include a reference electrode in the form of, e.g., an Ag/AgCl layer, thus providing a familiar electrochemical reference.

The sandwich structure of this embodiment may be laminated, e.g. by a standard office laminator. Typically, a temperature of 85° C. would be used during lamination if the plastic film material is PET for example. Alternatively, the layers may be adhered together using any suitable adhesive.

One of the important attributes of this embodiment is that it is inherently manufacturable, since it consists of three parts only that can be easily made and joined together. The lower layer can also be functionalised with a wide variety of enzymes.

Of course, the lower layer could comprise an array of patches 2 as in the second embodiment.

Figure 7:
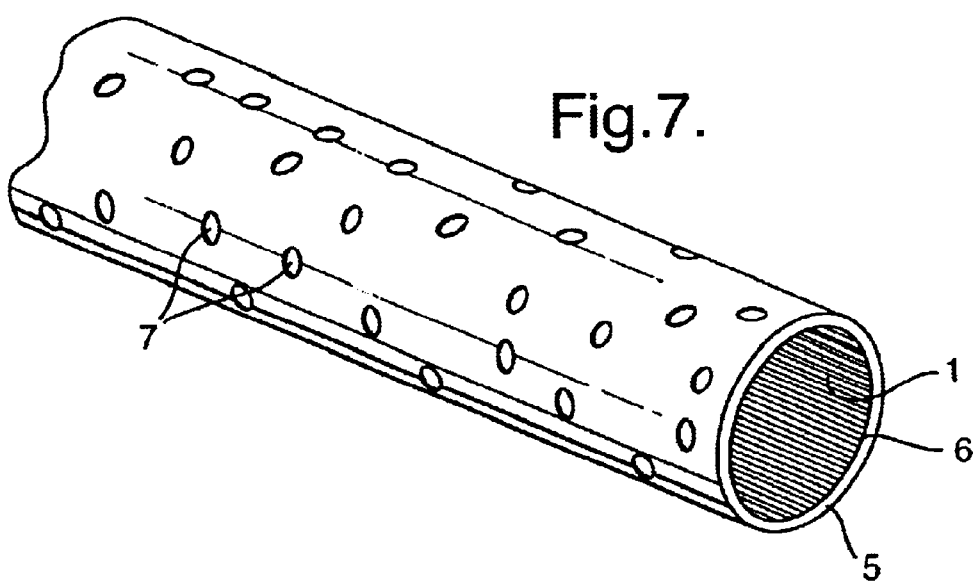
FIG. 7 is a perspective view of a fourth embodiment.

FIG. 7 shows a fourth embodiment of the invention that takes the form of a wire or filament. Here, the substrate 1, the conducting area 6 and the dielectric ink 5 are wrapped in a cylindrical configuration. The counter electrode is not shown.

In each embodiment, the conducting area 6 may be formed by a conventional technique such as screen printing, spin or dip coating, meniscus coating or spray coating an ink, for example.

Alternatively the layer can be formed in situ by chemical reaction, for example by heating a carbonaceous material to convert it to carbon. Thus it may be formed by spin coating a concentrated solution of sugar such as glucose, mixed with a catalyst, followed by heat treatment up to 900° C. to carbonize the layer. The catalyst typically is 5% by weight of zinc chloride and with this process a highly conductive (resistivity of about 0.2 ohm cm) glassy film of carbon of around a micron in thickness is formed on the substrate. Similarly, the dielectric area 5 may be formed by conventional techniques, e.g. from silicon nitride using standard semiconductor processing techniques, or by the use of a commercially available dielectric ink.

The pores 7 may be formed by conventional means, e.g. by photolithography when the dielectric layer is applied, or afterwards by laser or energetic particle bombardment or by means of a particulate fluid as described in more detail below.

Functionalisation or activation of the micro-electrodes with biopolymers can be done by various methods. When carbon surfaces are used as the conducting surfaces, the biopolymer may be immobilised on the carbon surface directly. Preferably it is covalently bonded to the carbon surface, although simple physical absorption is also possible, particularly for disposable devices. However, in general, it is usual to either modify the surface e.g. by oxidation to produce negatively charged sites that interact with positively charged sites on the enzyme or to attach a layer of linker molecules to the conducting surface to facilitate charge transfer between the electrode and the biopolymer. This can be further modified by changing the concentration of positively charged cations in the environment, for example by having present a cationic species, poly L-lysine. This is generally necessary when the conducting surface is of a metal such as gold or copper-Kapton (polyimide) or other metal-on-polymer film that can be patterned by photographic/electrolytic methods.

A typical linker molecule might be poly L-lysine. The chosen biopolymer can be introduced on to the conducting patch via a capillary probe using a modified probe station. Generally, the biopolymer is mixed in a buffer solution before application to the patch. The concentration of the biopolymer in the buffer solution is not critical but is suitably sufficient to give a monolayer coverage of the micro electrode surface.

If made thin enough, each embodiment can give a flexible multi-micro electrode assembly that can be applied directly to the skin, for example. In some instances, the flexible biosensor may be kept in place on the skin using an adhesive. This type of sensor is ideal for the detection of substances in body fluid.

Each device is designed to be plugged into an electrochemical potentiostat. Usually, a constant potential difference would be applied between the counter electrode 3 and carbon patch 2. The current that flows between them (i.e. through the liquid to be assessed) can then be measured. Potential differences up to 1V can generally be used. However, any voltage of at least about 150 mV is usually sufficient to ensure that operation occurs in a desirable area of the current-voltage characteristic curve where the current reaches a "plateau". Typical currents to be measured are in the range of 0.1 to 1 nA so that they can be measured using standard equipment.

The structure of the second embodiment shows improved flexibility over the first embodiment. On the one hand, eight different biopolymers could be employed, one on each patch, to detect eight different analytes, or alternatively each patch could be activated with the same biopolymer and eight different types of electrochemical measurements made simultaneously. Manifestly, the number of micro-electrode arrays could be more or less than eight.

Each embodiment will permit the use of mediated enzyme action i.e.: a mediator such as ferrocene can be associated with the biopolymer to act as a "shuttle" molecule in order to facilitate the transfer of electrons from the biopolymer to the conducting surface although the preferred method of expressing the electro-analytical response is by direct electron transfer between the enzyme and the micro electrode.

Figure 6A:
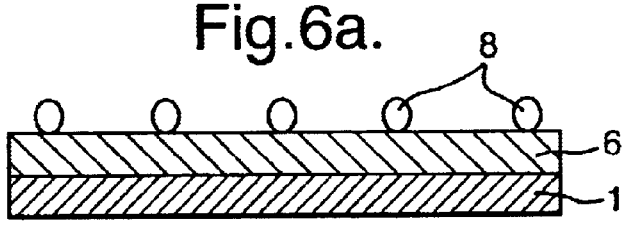
FIGS. 6a–c show successive steps of one way to make the dielectric coating.
Figure 6B:
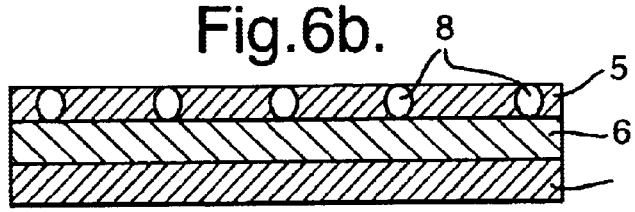

As discussed above, the dielectric layer 5 may be produced using any conventional technique. The following method, which also forms part of the present invention, has been found to be particularly advantageous. The conducting surface 6 is firstly coated with a plurality of particles 8 as shown in FIG. 6a. The particles are sized so that their diameter is approximately the same as the required final thickness of the dielectric layer 5 and also of the pores 7. They are also applied in such numbers so as to yield the required spacing between micro electrodes. After the particles have been applied, a layer of insulator (dielectric) 5 is sprayed onto the conducting surface 6 as shown in FIG. 6b.

As an alternative to this, a fluid composition containing suspended particles may be used, i.e. desirably, the particles and the fluid dielectric are premixed and are applied to the conducting substrate at the same time. Referring to FIG. 6b, the alternative method comprises applying the particles 8 and fluid 5 at the same time.

Figure 6C:
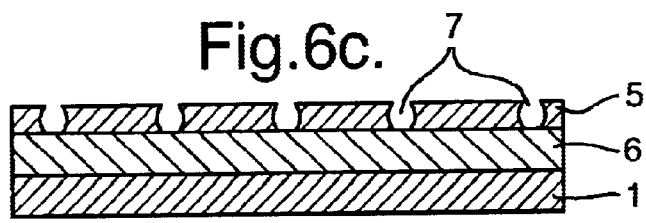

Thus, a conducting electrode 6, which may be of metal e.g. gold or of carbon, carries an overlying coating layer 5 of a dielectric ink containing suspended particles 8. After drying the coating layer, the particles are removed to leave the structure shown in FIG. 6c where the array of particles 8 has been replaced by an array of holes 7 which reveal the conducting substrate 6 and define micro-electrodes. The biopolymer is then applied to the pores 7 so as to functionalise the device. Of course, the biopolymer could be applied first to the bare conducting surface.

The fluid composition may be a dielectric ink, such as the commercially available materials which can be applied as a liquid by a variety of standard coating methods as described earlier and which can be cured (via either ultra-violet, chemical or heat treatment for example) to form a solid insulating dielectric layer. The suspended particles may be of glass or preferably of a polymer such as polymethylmethacrylate, polystyrene or polyethylene oxide. Alternatively the fluid composition may be in the form of an inorganic colloid. The size and volume fraction of the particles in the dielectric ink determine the diameter and frequency of the micro-electrodes in the array.

When the particles are water soluble they can be removed by dissolution. If they have a lower combustion point than the dielectric, they can be removed by ashing in an oven or plasma reactor.

In the most preferred method, the dielectric coating 5 comprises a layer of silica which may be formed using a sol-gel layer made from tetraethylorthosilicate (TEOS). The holes 7 may be created by mixing polymer spheres 8 (preferably of polystyrene) into the gel prior to spin coating onto the glassy carbon layer 6. The gel is then heated to around 700° C. which causes the polymer beads to dissociate leaving holes in the cured dielectric constituting the microelectrodes.

What is claimed is:

1. A biosensor comprising a conducting surface, a layer of dielectric material overlying the conducting surface, a plurality of micro electrodes constituted by a plurality of pores extending through the thickness of said dielectric layer, each pore being separated from its neighbour, a biopolymer positioned in said pores, and a counter electrode arranged such that electrical connection can be made between it and at least part of said conducting surface by a fluid to be assessed.

2. A biosensor according to claim 1 wherein said conducting surface comprises a carbon surface.

3. A biosensor according to claim 1 or claim 2 wherein said biopolymer is attached to said conducting surface via a linker molecule.

4. A biosensor according to claim 1 or 2 wherein the biopolymer is associated with a mediator to facilitate the transfer of electrons from said biopolymer to said conducting surface.

5. A biosensor according to claim 1 or 2 wherein said conducting surface comprises two or more areas of conducting material.

6. A biosensor according to claim 5 wherein said areas of conducting material are arranged in a substantially uniform formation.

7. A biosensor according to claim 1 wherein the biosensor is flexible.

8. A biosensor according to claim 1 further comprising means for retaining said fluid in said pores.

9. A biosensor according to claim 8 wherein said means for retaining said fluid comprises a polymer wall.

10. A biosensor according to claim 8 wherein said means for retaining said fluid comprises a layer of permeable material.

11. A biosensor according to claim 10 wherein said counter electrode comprises a perforated conducting sheet, and the layer of permeable material is between the perforated conducting sheet and the dielectric layer.

12. A biosensor according to claim 1 wherein said conducting surface and said counter electrode are arranged on a single insulating substrate.

13. A biosensor according to claim 1 wherein said counter electrode comprises a perforated conducting sheet.

14. A biosensor according to claim 1 wherein said biopolymer is an enzyme.

15. A method of making a biosensor comprising the steps of:

providing a conducting surface;

providing a layer of dielectric material adjacent to said conducting surface, said dielectric material comprising a plurality of pores extending through the thickness of the dielectric layer;

each pore being separated from its neighbour;

providing a biopolymer in said pores; and providing a counter electrode insulated from said conducting surface.

16. A method according to claim 15, wherein a substrate layer is provided adjacent to said conducting surface.

17. A method according to claim 15 or claim 16 further comprising the step of providing a layer of permeable material adjacent to said dielectric layer.

18. A method according to claim 17 further comprising the step of adhering said layers together.

19. A method according to claim 15, wherein the layer of dielectric material is made by applying to said conducting surface particles of substantially the same diameter as said pores;

applying a dielectric in the form of a fluid containing it to said conducting surface;

allowing said fluid to dry; and removing said particles.

20. A method according to claim 19 wherein said particles and said fluid dielectric are premixed and are applied to said conducting substrate at the same time.

21. A method according to claim 19 or claim 20, wherein said particles are water soluble and are removed by dissolution in water.

22. A method according to claim 19 or claim 20, wherein said particles are removed by heat treatment.

23. A method according to claim 15, wherein the biosensor is one as claimed in claim 1.

24. A biosensing system comprising:

a current measuring device;

a potential difference generator; and a biosensor as claimed in claim 1 or made by the method of claim 15;

wherein said potential difference is applied by said potential difference generator between the counter electrode and the conducting surface of said biosensor and, said current measuring device is configured to measure a current flowing between said counter electrode and said conducting surface.

* * * * *